United States Patent [19]

Glassman

[11] Patent Number: 4,683,231
[45] Date of Patent: Jul. 28, 1987

[54] METHOD OF PREVENTING WITHDRAWAL SYMPTOMS ASSOCIATED WITH THE CESSATION OR REDUCTION OF TOBACCO SMOKING

[75] Inventor: Alexander H. Glassman, Teaneck, N.J.

[73] Assignee: Research Foundation for Mental Hygiene, Inc., New York, N.Y.

[21] Appl. No.: 852,650

[22] Filed: Apr. 16, 1986

Related U.S. Application Data

[62] Division of Ser. No. 585,900, Mar. 2, 1984, Pat. No. 4,588,739.

[51] Int. Cl.$^4$ ............................................. A61K 31/395
[52] U.S. Cl. ..................................... 514/220; 514/813
[58] Field of Search ................................. 514/813, 220

[56] References Cited

U.S. PATENT DOCUMENTS 4,575,510  3/1986  Sjoerdsma .......................... 514/813

*Primary Examiner*—Stanley J. Friedman
*Attorney, Agent, or Firm*—John P. White

[57] ABSTRACT

In human subjects accustomed to smoking tobacco the withdrawal symptoms associated with the cessation or reduction of tobacco smoking may be prevented by administering to the subject an effective amount of an alpha-2 adrenergic agonist such as clonidine hydrochloride for a suitable period of time.

Alternatively, such withdrawal symptoms may be prevented by administering to such a person an effective amount of alprazolam.

7 Claims, 2 Drawing Figures

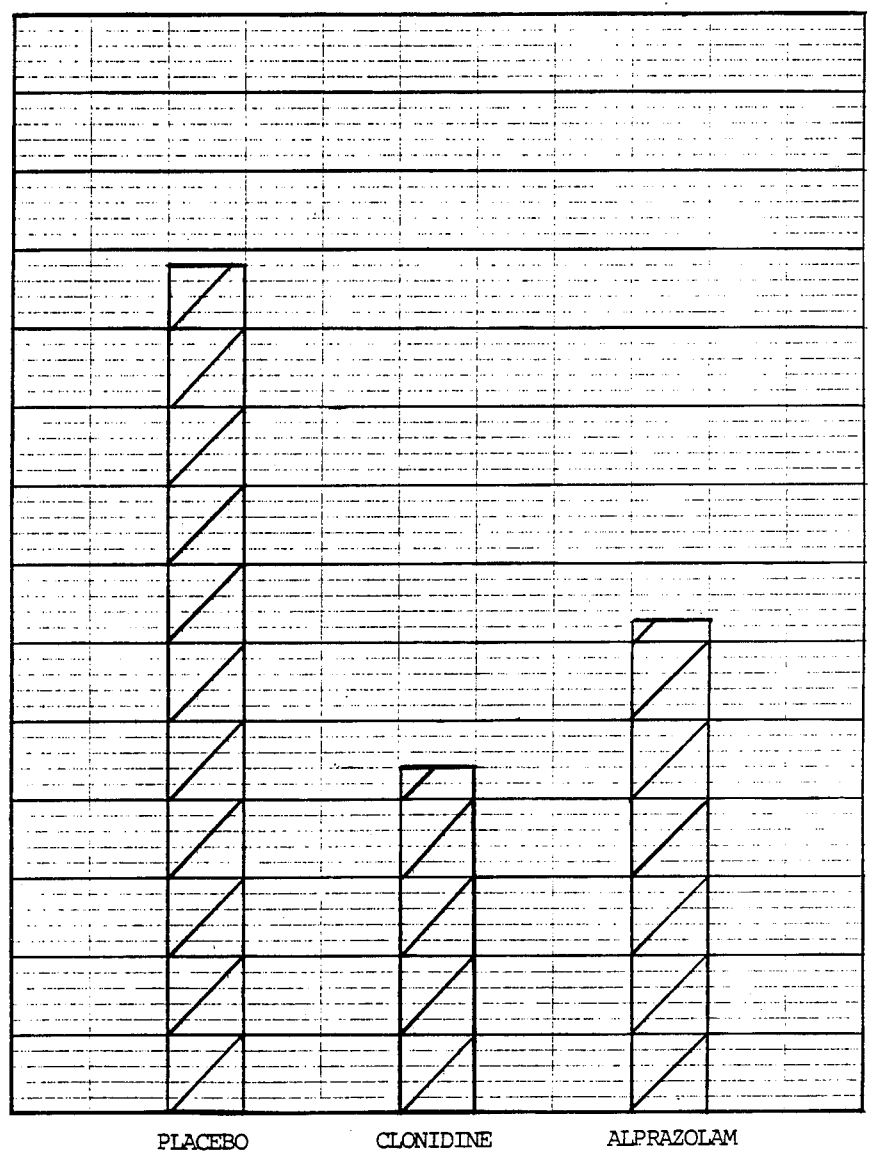

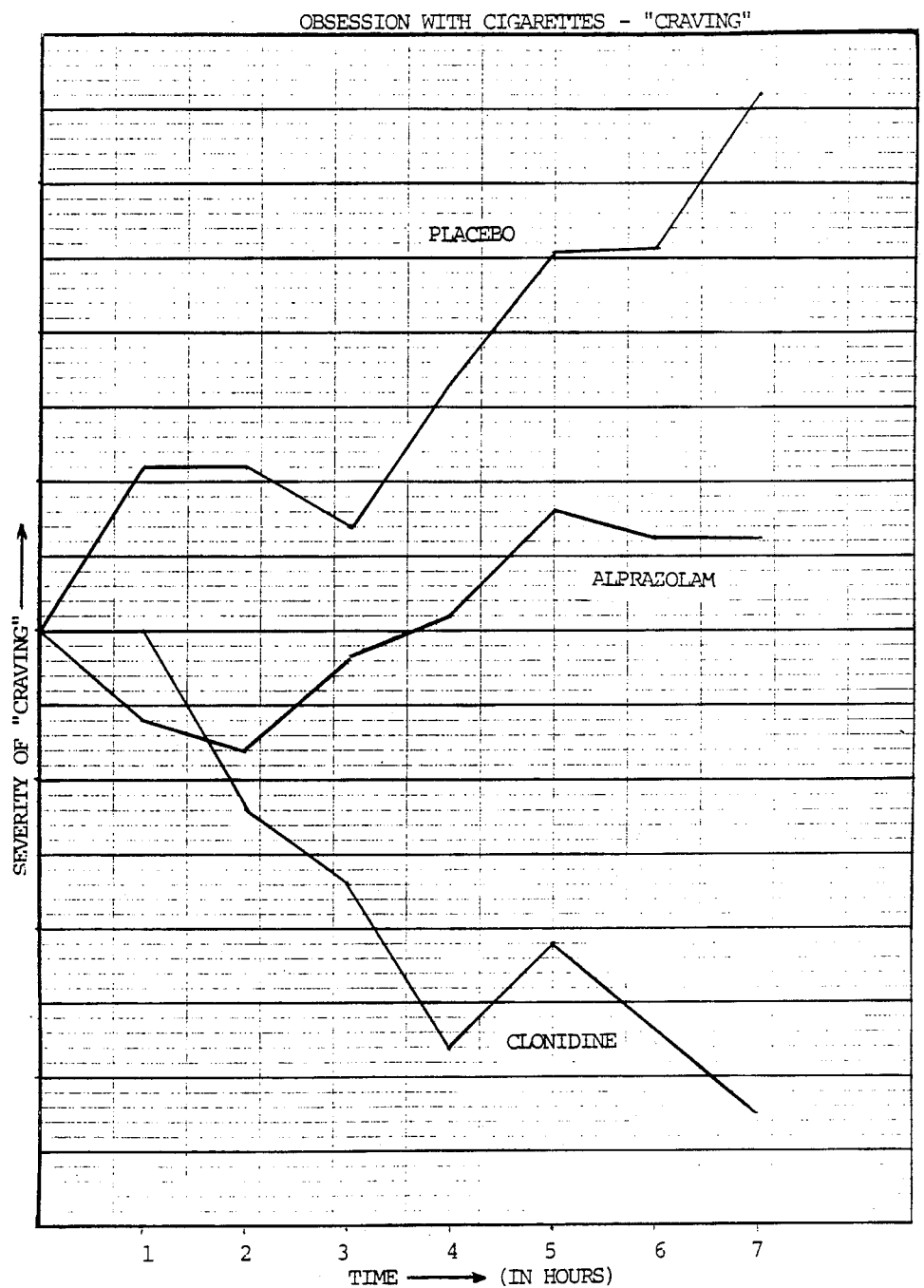

METHOD OF PREVENTING WITHDRAWAL SYMPTOMS ASSOCIATED WITH THE CESSATION OR REDUCTION OF TOBACCO SMOKING

This application is a division of U.S. Ser. No. 585,900, filed Mar. 2, 1984, now U.S. Pat. No. 4,588,739.

BACKGROUND OF THE INVENTION

Within the description which follows various publication are referenced by arabic numerals. Full citations for these publications may be found at the end of the specification immediately preceding the claims. The disclosures of these publications in their entireties are hereby incorporated by reference into this application in order to more fully describe the state of the art to which this invention pertains.

In 1978, Gold, Redmond and Kleber demonstrated that clonidine dimished the opiate withdrawal syndrome in chronically addicted human subjecs (1). Clonidine is a presynaptic alpha-2 noradrenergic agonist. Central noradrenergic function had previously been implicated in the action of opiates without anatomical specificity since the 1960's (2, 3). By the mid-1970's, evidence accumulated indicating that a major anatomical connection between the central adrenergic and opiate systems existed in a small nucleus of the dorsal pons. the locus coeruleus. This nucleus accounts for nearly half of the noradrenergic neurons and produces the majority of norepinephrine in the mammalian brain (4). These adrenergic cells are densely populated with opiate receptors (5), and either enkaphalins (6, 7) or opiates (8, 9) and alpha-2 adrenergic agonists (10, 11) decreased their firing rate. Opiate withdrawal results in a marked increase in this firing rate (12). Extensive data has now accumulated in both animals (13, 14, 15, 16) and man (17, 18, 19, 20) confirming Gold's observation that clonidine diminishes opiate withdrawal syndromes and that the diminished withdrawal behavior is related to the diminished firing rate in the adrenergic nuerons (21). The present invention relates to the discovery that alpha-2 adrenergic agonists such as clonidine markedly after the acute withdrawal syndrome associated with cigarette smoking and suggests that central adrenergic overactivity is a common feature in the pathophysiology of withdrawal syndromes seen with cigaretts, alcohol and opiates. The invention also relates to the discovery that such withdrawal symptoms may be prevented by alprazolam.

SUMMARY OF THE INVENTION

In human subjects accustomed to smoking tobacco the withdrawal symptoms associated with the cessation or reduction of tobacco smoking may be prevented by administering to the subject an effective symptom-preventing amount of an alpha-2 adrenergic agonist such as clonidine hydrochloride for a suitable period of time. Preferably, administration is oral, the effective amount is an amount between about 0.02 and 2.0 mg daily and the period of administration is from about 3 to 6 weeks.

Although less preferred, the withdrawal symptoms associated with the cessation or reduction of tobacco smoking may alternatively be prevented by administering to a smoker an effective amount of alprazolam, i.e., from about 0.1 to 10 mg daily, for a suitable period of time, e.g., about 3 to 6 weeks.

BRIEF DESCRIPTION OF THE FIGURES

FIG. 1 shows the global ratings obtained at the end of each experiment day, double-bind, assessing the difficulty in not smoking. A 100 mm line was used with 10 being extremely difficult not to smoke and zero being no thoughts or desire to smoke. Clonidine hydrochloride was significantly better than placebo ($p<0.001$) as was alprazolam ($p<0.05$). The difference between clonidine and alprazolam just failed to reach significance ($p<0.1$).

FIG. 2 shows the severity of craving plotted on an hourly basis during the first seven hours of treatment with clonidine, alprazolam and placebo.

DETAILED DESCRIPTION OF THE INVENTION

The withdrawal symptoms associated with cessation or significant reduction in tobacco smoking, e.g., cigarette smoking, in a human subject accustomed to regular or habitual smoking may be prevented or avoided by administering to the subject an effective symptom-preventing amount of an alpha-2 adrenergic agonist for a suitable period of time.

Although the detailed experimental results which follow concern clonidine hydrochloride, one of ordinary skill in the art to which the invention pertains would understand the results to apply to alpha-2 agonists generally (22). Such alpha-2 agonists include in addition to clonidine hydrochloride, guanabenz acetate, guanfacine, lofexidine, xylazine, tiamenidine, α-methyl-norepherine, azepexole, indoramin, 6-allyl-2-amino-5,6,7,8-tetrahydro-4H-thiazolo [4, 5-d] azepine diHCl and analogs thereof.

The alpha-2 adrenergic agonist may be administered by various known methods such as orally or intravenously. The presently preferred method is oral administration. The effective amount of alpha-2 adrenergic agonist may be any amount from about 0.001 to about 10.0 mg administered daily, preferably from about 0.02 to about 2.0 mg. The presently preferred amount of clonidine hydrochloride is about 0.1–1.0 mg, e.g. about 0.2 mg. Desirably, the alpha-2 adrenergic agonist is administered int wo or three doses, each succeeding dose being preferably given about 4 to 8 hours after the preceding dose. Administration of the alpha-2 adrenergic agonists is continued for a suitable period of time to accomplish the desired result. Presently, the preferred suitable time period is about 3 to 6 weeks.

As an alternative to the administration of an alpha-2 adrenergic agonist such as clonidine hydrochloride, this invention also contemplates the use of alprazolam. Thus, the invention also provides a method of preventing in a human subject accustomed to smoking tobacco the withdrawal symptoms associated with the cessation or reduction of tobacco smoking which involves administering to the subject an effective symptom-preventing amount of alprazolam for a suitable period of time.

Preferably, the alprazolam is administered orally and daily in two or three doses each of which is administered within 4 to 8 hours after the preceding dose, the daily amount administed being from about 0.1 to 10.0 mg. preferably about 0.5 to 2.0 mg, e.g. about 1 mg, for about 3 to 6 weeks.

The following experimental details are set forth to aid in an understanding of the invention but are not intended to, and should not be construed so as to, limit in any way the invention as defined by the claims which follow hereinafter.

EXPERIMENTAL DETAILS

Methods

Individuals smoking more than 30 cigarettes per day were recruited to participate in a double-blind, triple crossover study of the effects of an alpha-2 adrenergic agonist on the acute smoking withdrawal syndrome. In addition to a placebo control, a benzodiazapine-like drug, alprazolam, was used as the third experimental condition. At the dosing ratio of ten to one, alprazolam has been shown to be equally anxiolytic and slightly less sedative than diazepam (23) in anxious medical patients.

All subjects were in good health and were drug-free except for two female volunteers who used medication for birth control. All subjects were instructed to refrain from smoking for twenty-four hours on three separate occasions. On each occasion they were told not to smoke after going to bed and to report without smoking at 8:30 AM the next morning. Baseline pulse, blood pressure and psychological measures were obtained over the next 30 minutes and the one of three treatment regimens was begun. Subjects received either clonidine hydrochloride 0.2 mg (Catapres ®, Boehringer Ingelheim Ltd, Ridgefield, Conn.), alprazolam 1.0 mg (Xanax ®, the Upjohn Company, Kalamazoo, Mich.), or placebo in a randomly assigned sequence. On the two subsequent experimental days subjects received the remaining two treatments, again in a random sequence. All treatments were given in two divided doses with the second dose coming 90 minutes after the first. Pulse and blood pressure, including orthostatic blood pressure, were measured every 90 minutes. At the same time, subjects completed a series of eight analogue scales. These scales made use of a 100 mm line to assess tenseness, anxiety, irritability, jitteriness, depressed mood, craving to smoke, thoughts about smoking and the desire to "munch". At the end of each experimental day, subjects assessed the degree to which the experimental treatment had helped them to do without cigarettes and rated this on a scale from 1-10.

In order to avoid crossover effects, subjects were asked to resume their normal smoking pattern after each experimental day. A minimum of four normal smoking days separated each experimental day. After the third session, each subject was offered a two-week trial with the experimental treatment of his or her choice.

Global ratings of the difficulty in not smoking were compared by means of T tests. Treatment effects on individual scales were obtained by averaging the scale scores during the period from the first to the sixth hour after the first doses. These averages were compared by ANOVA. Because it was not clear that these scale scores represented interval measurements, they were converted to rankings and the more conservative Friedman non-parametric two-way analysis of variance was performed.

RESULTS

Fifteen subjects completed all three experimental days. Table I describes the characteristics of the sample. Thirteen of 15 subjects showed a clear preference for the drug condition during the acute phase of smoking withdrawal ($p > 0.001$). Of the two subjects who did not benefit from medication, one showed only very modest withdrawal symptoms int he placebo condition and could not distinguish between the drug and placebo conditions, in spite of a history of smoking 1½ packages of cigarettes per day. The only other subject who did not prefer drug treatment manifested marked withdrawal symptoms during the placebo period and experienced no relief from either drug. She also showed no significant effect of clonidine on pulse or blood pressure. The fifteen subjects' global assessments of the difficulty in not smoking, made at the end of each experimental day, is shown in FIG. 1. Conidine ($p < 0.001$) and alprazolam ($p < 0.05$) are significantly better than placebo, and there is a trend for subjects to prefer clonidine ($p < 0.1$) over alprazolam. Of the thirteen subjects that found drug treatment effective, ten preferred clonidine ($p < 0.05$).

TABLE I

| Age | Sex | Packs/Day | Cigarettes/Day | Years Smoking | Withdrawal Symptoms | Medical Illness | Meds | Drug |
|---|---|---|---|---|---|---|---|---|
| 27 | M | 1-2 | 20-40 | 10 | craving nervous | — | — | EtOH |
| 31 | F | 1½-3 recent 3 | 60 | — | anxiety irritable craving | — | — | occas. EtOH |
| 46 | F | 2-3 | 40-60 | 25 | irritable anxiety | Mild hypertension | — | occas. EtOH |
| 35 | F | 2½ | 50 | 17 | craving irritable tension | — | — | occas. EtOH |
| 41 | F | 1 | 20 | — | craving irritable | — | — | — |
| 40 | F | 1½ | 30 | — | irritable moody ↑ appetite | — | — | occas. EtOH |
| 45 | F | 1½-2 | 30-40 | 20 | craving anxiety irritable | — | Premann | — |
| 31 | F | 1½ | 30 | 15 | craving irritable ↑ weight | — | — | EtOH |
| 36 | M | sl > 2 | 45 | 21 | irritable demanding wants to do something with hands | hypertension | — | EtOH |

TABLE I-continued

| Age | Sex | Packs/Day | Cigarettes/Day | Years Smoking | Withdrawal Symptoms | Medical Illness | Meds | Drug |
|---|---|---|---|---|---|---|---|---|
| 25 | F | 2 | 40 | 8 | craving irritable ↑appetite | — | PCP | EtOH |
| 34 | F | 2 | 40 | 17 | craving irritable | — | — | EtOH |
| 32 | F | 1–1½ | 20–30 | 17 | never tried to quit | — | — | EtOH |
| 41 | F | 1½–2 | 30–40 | 24 | ↑appetite irritable ↓sleep | h/o RA Myxcma | — | EtOH |
| 20 | F | 1 | 20 | 5 | craving tension | — | — | occas. EtOH |
| 25 | F | 1½–2 | 30–40 | 10 | craving anxiety tension | — | — | EtOH |

The analyses of the visual analog scores on the scales for anxiety, irritability, craving, restlessness, concentration, sadness, tenseness, and drowsiness, are presented in Table II. There are significant treatment differences in seven of the nine scales using a parametric analysis, and in five of nine using a non-parametric test. In spite of the trend for subjects to prefer clonidine over alprazolam on the global ratings, the individual item did not distinguish between the two drug treatments. On anxiety, irritability, concentration, and tenseness, both drugs were clearly better than a placebo and essentially identical to each other. Even the two most common side effects, drowsiness and dizziness, did not differ between the two drugs. Only the scale measuring craving (thinking about or wish to smoke) reflected the strong tendency in the global ratings for subjects to prefer clonidine. Here clonidine was significantly more effective than both placebo (p<0.004) or alprazolam (p<0.02). On this measure there was only a trend for alprazolam (p<0.06) to be more effective than placebo.

Previous studies of smoking withdrawal syndrome have shown that "craving" is the most consistent withdrawal symptom (24) and that it tends to be minimal in the morning and to increase as the day progresses (25, 26). For that reason we plotted the hourly rating for craving during the first seven hours of treatment. This corresponds essentially to a period from 9:30 AM until 4:30 PM (see FIG. 2). Displayed in this manner, there is a trend for clonidine to be better than placebo during the second and third hour of drug treatment. This difference reaches significance in the early afternoon and remains significant over the next three hours.

As would be expected (27), clonidine produced a significant decrease in both pulse (p<0.01) and blood pressure (p<0.001).

This decrease in blood pressure is correlated significantly with the decrease in craving (r=0.65) and with global change (r=0.48) on clonidine.

TABLE II

| SCALE | TREATMENT | | | ANOVA | | FRIEDMAN | |
|---|---|---|---|---|---|---|---|
| | CLONIDINE | ALPRAZOLAM | PLACEBO | F | P | FTS | P |
| ANXIETY | 1.46 | 1.54 | 2.94 | 4.53 | .024* | 4.14 | .12 |
| IRRITABILITY | 2.20 | 2.04 | 3.91 | 5.34 | .014* | 7.09 | .03* |
| CRAVING | 3.23 | 4.97 | 6.03 | 9.77 | .001* | 8.91 | .01** |
| RESTLESSNESS | 1.60 | 1.63 | 3.09 | 3.69 | .043* | 4.14 | .12 |
| CONCENTRATION | 2.17 | 1.72 | 2.27 | 0.05 | .948 | 0.59 | .74 |
| TEARFUL | 0.83 | 0.83 | 0.72 | 0.04 | .957 | 3.32 | .19 |
| TENSION | 1.51 | 1.51 | 3.12 | 5.09 | .016* | 8.77 | .01** |
| DROWSY | 5.06 | 4.41 | 1.13 | 13.10 | .001** | 13.64 | .001** |
| DIZZY | 2.58 | 2.04 | 1.15 | 8.82 | .006** | 7.95 | .02 |

DISCUSSION

Although clonidine and alprazolam both reduce the acute withdrawal syndrome following sudden abstinence in heavy cigarette smokers, subjects preferred clonidine. Clonidine had significantly more effect on "craving" than alprazolam. Clonidine is regularly used in opiate withdrawal at two to five times the doses used here (17, 18, 19, 20) and similarly, higher doses of alprazolam are used in the treatment of both panic disorder and depression. Maximizing either the dose or the dosing interval might have improved the response with either treatment. The correlations between blood pressure and both global response (r=0.4) and craving (r=0.6) could stem from those subjects with an adequate plasma concentration of clonidine. The blook pressure effects of clonidine have been correlated with the drug's plasma concentration (28). Plasma clonidine concentrations were not measured and this could account for some of the inter-subject variability. If that is so, the efficacy of clonidine may be even stronger than these data suggest. It is also not possible to ascertain from these experiments if differences in efficacy between the drugs would develop if the period of abstinence was extended beyond eighteen hours.

These limitations of the experimental design notwithstanding, the acute effects of clonidine, particularly on craving, were striking. This does not imply that these drugs are a cure for smoking. Multiple studies have shown that even among those smokers who have successfully withdrawn from cigarettes, a high percentage will return to cigarettes within the next six months (24, 29, 30). Nevertheless, that any drug could enable heavy smokers to quickly and asymptomatically abstain, would undoubtedly be useful to many smokers. Our uncontrolled clinical experience suggests that clonidine continues to be effective for at least two weeks. Subjects were generally not maintained for longer periods of time. Most subjects who chose to continue treatment following the initial experiment period preferred clinidine. We, therefore, have little experience with alprazolam beyone the initial 24-hour period.

After we began these studies of smoking withdrawal, we learned of several studies reporting on the use of clonidine in the treatment of alcohol withdrawal (31, 32, 33, 34). These studies were initially undertaken in an effort to control the hypertension associated with alchoholic withdrawal, but there seems little question that, here too, clonidine suppresses a significant portion of the withdrawal syndrome. Recent animal data also support the role of noradrenergic overactivity in alcoholic withdrawal (35). Taken together, the data with opiates, alcohol and cigarettes strongly suggest a common pattern of central adrenergic overactivity in these withdrawal syndromes.

As has already been noted, the locus coeruleus is the major source of noradrenergic cell bodies (4). In addition to its association with opiate receptors and opiate withdrawal, the locus has been put forward as a central "alerting alarm" system (36). Drugs that decrease the firing rate of the locus, such as benzodiazepines, opiates and clonidine, have marked sedative or tension reducing activity (37), and drugs that increase its firing rate such as piperoxane and yohimbine, increase anxiety (38, 39). Moreover, electrical stimulation (40) and ablation (41) experiments involving the locus have produced results consistent with this alerting alarm function. It would be tempting to conceive of tension-reducing substances such as opiates or alcohol, acting by reducing the firing rate of the locus, and of the withdrawal of these substances, after chronic administration, resulting in a rebound over-firing of the locus. It would even be easy to conceive of characteristic withdrawal craving as a conditioned response to modest increases in locus firing while more marked increases would be associated with the unconditioned increase in tension and anxiety. However, there is far from universal agreement about the role of the locus in anxiety (42, 43), and even the role of the locus in opiate withdrawal is unquestioned (44).

Nevertheless, the clinical observations of clonidine's efficacy in opiate, alcohol and cigarette withdrawal, forces on us the question of what these withdrawal syndromes share in common. Certainly, on clinical grounds, the alcoholic withdrawal with delirium tremens, hallucinations and epileptiform fits, would not easily be mistaken for the agitation, muscular cramps, and wretching of opiate withdrawal, let alone for the tense and irritable abstinent smoker. However, before these end-stage differences come to dominate the clinical picture, the early withdrawal as well as the dependence process itself share a number of pharmacological and behavioral characteristics (45). Over twenty years ago, Wikler wrote that the maintenance of opioid-taking behavior is most dependent on the intense craving of the drug associated with the onset of withdrawal (46). Both Wolfe (47) and Gross (48) noted alcohol withdrawal always begins and usually consists, not of D.T.'s and fits, but of sleeplessness, "bad nerves" and the "need" for a drink. In our fifteen abstinent subjects, as in other smokers that have been studied (24), the most consistent and most severe withdrawal symptom is "craving". By craving we mean a preoccupation with thoughts about, or an urge for, the habituating substance, not necessarily associated with any physical distress. It would seem obvious that this drug craving, or preoccupation, is a common denominator across these habituations and plays an important role in maintaining the habituation.

I would be easy to assume that a craving for a tension reducing drug develops in the absence of the drug because the addict experiences a rebound dysphoria, and craves the drug to eliminate that dysphoria. But that is not the observation. Craving is the earliest, the most consistent and severe symptom of cigarette withdrawal. It is also specifically responsive to clonidine in the sense that clonidine's ability to diminish craving did not depend on the presence of, or reduction in, anxiety, irritability or tension. A number of subjects were essentially without these dysphoric symptoms and still experienced a substantial reduction in craving. Clonidine and alprazolam both reduced anxiety, irritability, restlessness, and tension to an almost identical degree, and both produced an equal degree of drowsiness; yet clonidine had significant more effect on craving.

Clonidine is an alpha-2 agonist and at low or modest doses selectively decreases noradrenergic activity (49). Thus, the selectivity of clonidine for both craving and noradrenergic activity would suggest a special relationship between craving and central noradrenergic function. The link between the central adrenergic system and withdrawal symptoms is appealing both because of the hypothesized relationship between noradrenergic function and anxiety and the known relationship between increasing stress and increasing central noradrenergic activity (50). Even if the locus is not directly involved in the mediation of anxiety, its relationship to attention and novel stimuli (51) make it likelty that increased activity of the locus is, at least, regularly associated with anxiety producing stimuli. The increased firing rate of either a central noradrenergic alarm system or a noradrenergic system whose activity regularly predicts alarm, could be paired to a substance that suppresses its activity, and result in a conditioned craving for that tension-reducing substance with increasing noradrenergic activity. This model is consistent with our experimental observation in that although both clonidine and alprazolam reduce locus firing, clonidine is known to have the more powerful pharamacological effect on locus firing (52).

Siegel has described tolerance conditioned to external environmental cues (53). He has shown that in morphine dependent animals, their tolerance to morphine overdose relates tot he environment in which they receive the overdoes (54). With other experiments he has extended this conditioned tolerance model to show that both withdrawal and drug craving can result from environmentally conditioned cues. We would suggest that the mechanism responsible for specific craving is the pairing of noradrenergic activity with the abused substance. Either the locus or some related set of brain stem noradrenergic nuclei that fire with increasing alarm or tension, can be paired to a substance that diminishes tension in such a way that this firing, even before it reaches the level of distress, produces a craving for that substance. Thus, the craving for the drug would occur with increasing noradrenergic activity whether that noradrenergic activity was induced by stress, environmentally conditioned cues, or noradrenergic rebound during drug withdrawal. This would help to explain the tenaciousness of drug abuse in that craving can result from many sources beyond the original pharmacological tolerance of the receptor for the drug. As a matter of fact, it is unnecessary to limit this model to habituating substances; behaviors such as nail biting or binge eating could have the tension reducing effects on this central alarm system and could be habituating with a similarly conditioned craving for the behavior.

REFERENCES

1. M. S. Gold, D. E. Redmond, Jr., and H. D. Kleber: Clonidine blocks acute opiate-withdrawal symptoms. Lancet II: 599–601, 1978.
2. L. M. Gunne: Catecholamines and 5-hydroxtryptamine in morphine tolerance and withdrawal. Acta Physiol. Scand. 58, Suppl. 204: 1–91, 1963.
3. E. L. Way and F. H. Shen: Catecholamines and 5-hydroxytryptamine. In: Narcotic Drugs: Biochemical Pharmacology. D. H. Clouet, ed. Plenum Press, N.Y., 1971, pp. 229–253.
4. D. G. Amaral and H. M. Sinnamon: The locus coeruleus: neurobiology of a central noradrenergic nucleus. Prog. Neurobiol. 9: 147–196, 1977.
5. M. J. Kuhar: Histochemical localization of opiate receptors and opioid peptides. Fed. Proc. 37: 153–157, 1978.
6. W. S. Young, 3rd, S. J. Bird, and M. J. Kuhar: Iontophoresis of methionine-enkephalin in the locus coeruleus area. Brain Res. 129: 366–370, 1977.
7. P. G. Guyenet and G. K. Aghajanian: Excitation of neurons in the nucleus locus coeruleus by substances P and related peptides. Brain Res. 136: 178–184, 1977.
8. J. Korf, B. S. Bunney, and G. K. Aghajanian: Noradrenergic neurons: morphine inhibition of spontaneous activity. Eur. J. Pharmacol. 25: 165–169, 1974.
9. S. J. Bird and M. J. Kuhar: Iontophoretic application of opiates to the locus coeruleus. Brain Res. 122: 523–533, 1977.
10. T. H. Svensson, B. S. Bunney, and G. K. Aghajanian: Inhibition of both noradrenergic and serotonergic neurons in brain by the alpha-adrenergic agonist clonidine. Brain Res. 92: 291–306, 1975.
11. J. M. Cedarbaum and G. K. Aghajanian: Catecholamine receptors on locus coeruleus neurons: pharmacological characterization. Eur. J. Pharmacol. 44: 375–385, 1977.
12. G. K. Aghajanian: Tolerance of locus coeruleus neurones to morphine and supression of withdrawal response by clonidine. Nature 276: 186–188, 1978.
13. L. F. Tseng, H. H. Loh, and E. T. Wei: Effects of clonidine in morphine withdrawal signs in the rat. Euro J. Pharmacol. 30: 93–99, 1975.
14. D. R. Meyer and S. B Sparber: Clonidine antagonizes body weight loss and other symptoms used to measure withdrawal in morphine pelleted rats given naloxone. Pharmacologist 18: 236, 1976.
15. J. Vetulani and B. Bednarczyk: Depression by clonidine of shaking behaviour elicited by nalorphine in morphine-dependent rats. J. Pharm. Pharmacol. 29: 567–569, 1977.
16. S. Fielding, J. Wilker, M Hynes, M. Szewczak, W. J. Novick, Jr., and H. Lal: A comparison of clonidine with morphine for antinociceptive and antiwithdrawal actions. J. Pharmacol. Exp. Ther. 207: 899–905, 1978.
17. T. W. Uhde, D. E. Redmond, Jr., and H. D. Kleber: Clonidine suppresses the opioid abstinence syndrome without clonidine-withdrawal symptoms: A blind impatient study, Psychiatry Res. 2: 37–47, 1980.
18. M. S. Gold, A. C. Pottash. D. R. Sweeney, and H. D. Kleber: Opiate withdrawal using clonidine: A safe, effective, and rapid nonopiate treatment. JAMA 243: 343–346, 1980.
19. D. S. Charney and H. D. Kleberg: Iatrogenic opiate addiction: Successful detoxification with clonidine. Am. J. Psychiatry 137: 898–990, 1980.
20. A. M. Washton and R. B. Resnick: Clonidine for opiate detoxification: Outpatient clinical trials. Am. J. Psychiatry 137: 1121–1122, 1980.
21. A. C. Swann, J. D. Elsworth, D. S. Charney, D. M. Jablons, R. H. Roth, D. E. Redmond, Jr., and J. W. Maas: Brain catecholamine metabolites and behavior in morphine withdrawal. Eur. J. Pharmacol. 86: 167–175, 1983.
22. S. Z. Langer and N. B. Shepperson, J. Cardiovascular Pharmacology, vol. 4 (Suppl. 1) S35–S40, 1982.
23. K. Rickels. I., Csanalosi, P. Greisman, D. Cohen, J. Werblowsky, H. A. Ross, and H. Harris: A controlled clinical trial of alprazolam for the treatment of anxiety. Am. J. Psychiarty 140: 82–85, 1983.
24. S. M. Shiffman: the tobacco withdrawal syndrome., In: Cigarette smoking as a Dependence Process. Norman A. Krasnegor, ed. National Institute on Drug Abuse Research Monograph 23. DHEW Pub. No. (ADM) 79-800. Washington, D.C.: Supt. of Docs., U.S. Govt. Print. Off., 1979, pp. 158–184.
25. T. W. Meade and N. J. Wald: Cigarette smoking patterns during the working day. Br. J. Preventive Soc. Med. 31: 25–29, 1977.
26. R. M. Gilbert and M. A. Pope: Early effects of quitting smoking. Psychopharmacology 78: 121–127, 1982.
27. G. Onesti, A. B Schwartz, K. E. Kim et al.: Antihypertensive effect of clonidine. Circ. Res. 28: Suppl. 2: 53–69, 1971.
28. M. J. Hogan, J. D. Wallin, and L. C. Chu: Plasma clonidine concentration and pharmacologic effect. Clin. Pharmacol. Ther. 30: 729–734, 1981.
29. W. A. Hunt and D. A Bespalec: An evaluation of current methods of modifying smoking behavior. J. Clin. Psychol. 30: 431–438, 1974.
30. W. A . Hunt and J. D. Matarazzo: Three years later: Recent developments in the experimental modifications of smoking behavior. J. Abnorm. Psychol. 81: 107–114, 1973.
31. S. E. Bjorkquist: Clonidine in alcohol withdrawal. Acta Psychiatr. Scand. 52: 256–263, 1975.
32. J. Walinder, J. Balldin, K. Bokstrom, I. Karlsson, B. Lundstrom, and T. H. Svensson: Clonidine suppression of the alcohol withdrawal syndrome. Drug and Alcohol Dependence 8: 345–348, 1981.
33. A. Nardoni, S. Baldissera, M. Iacono, R. Copetti, and R. Cella: La clondina nel trattamento della sindrome da astinenza alcoolica. Communicazione preliminare. Clin. Ter. 97: 619–624, 1981.
34. A. J. Wilkins, J. A. Steiner, and W. J. Jenkins: Efficacy of clonidine in the treatment of alcohol withdrawal states. Clin. Sci. 64 (2), Abstr 180: 64P, 1983.
35. W. Kostowski and E. Trazskowska: Effects of lesion of the locus coeruleus and clonidine treatment on ethanol withdrawal syndrome in rats. Pol. J. Pharmacol. Pharm. 32: 617–623, 1980.
36. D. E. Redmond, Jr., and Y. H. Huang: New evidence for a locus coeruleus-norepinephrine connection with anxiety. Life Sci. 25: 2149–2162, 1979.

37. M. S. Gold and D. E. Redmond, Jr.: Pharmacological activation and inhibition of noradrenergic activity alter specific behaviors in nonhuman primates. Neurosci. Abst. 3: 250, 1977.
38. J. M. Cedarbaum and G. K. Aghajanian: Noradrenergic neurons of the locus coeruleus: inhibition by epinephrine and activation by the alpha-antagonist piperoxane. Brain Res. 112: 413–419, 1976.
39. B. Scatton. B. Zivkovic and J. Dedek: Antidopaminergic properties of yohimbine. J. Pharmacol. Exp. Ther. 215: 494–499, 1980.
40. D. E. Redmond, Jr., Y. H. Huang, D. R. Snyder, and J. W. Maas: Behavioral effects of stimulation of the nucleus locus coeruleus in the stump-tailed monkey Macaca arctoides. Brain Res. 116: 502–510, 1976.
41. Y. H. Huang, D. E. Redmond, Jr., D. R. Snyder, and J. W. Maas: In vivo location and destruction of the locus coeruleus in the stumptail macaque (Macaca arctoides). Brain Res. 100: 157–162, 1975.
42. S. T. Mason and H. C. Febiger: Anxiety: The locus coeruleus disconnection. Life Sci. 25: 2141–2147, 1979.
43. S. T. Mason: Noradrenaline in the brain: Progress in theories of behaviourial function. Prog. Neurobiol. 16: 263–303, 1981.
44. K. T. Britton, T. Svensson, J. Schwartz, F. E. Bloom, and G. F. Koob: Dorsal noradrenergic bundle lesions fail to alter opiate withdrawal or suppression of opiate withdrawal by clonidine. Life Scr. 34: 133–139, 1984.
45. J. E. Henningfield. R. R. Griffiths, and Jasinski, D.R.: Human dependence on tobacco and opioids: common factors. In: Behavioral Pharmacology of Human Drug Depenence. T. Thompson and C. E. Johanson, eds. National Institute on Drug Abuse Research Monograph 37. DHHS Pub. No. (ADM) 81-1137. Washington, D.C.: Supt. of Docs., U.S. Govt. Print. Off., 1981.
46. A. Wikler: On the nature of addiction and habituation. Br. J. Addict. 57: 73–79, 1961.
47. S. M. Wolfe and M. Victor: The physiological basis of the alcohol withdrawal syndrome. In: Recent Advances in Studies of Alcoholism. N. K. Mello and J. H. Mendelson eds. U.S. Govt. Print. Off., Washington, D.C., 1972, pp. 188–199.
48. M. M. Gross. E. Lewis, and J. Hastey: Actute alcohol withdrawal syndrome. In: The Biology of Alcoholism. B. Kissin and H. Begleiter eds. Plenum Press, New York, 1974, pp. 191–263.
49. L. Isaac: Clonidine in the central nervous system: Site and mechanism of hypotensive action. J. Cardiovasc. Pharmacol. 2 (Suppl. 1): S5–S19, 1980.
50. J. Korf, G. K. Aghajanian, and R. H. Roth: Increased turnover of norepinephrine in the rat cerebral cortex during stress: role of the locus coeruleus. Neuropharm. 12: 933–938, 1973.
51. S. L. Foote, F. E. Bloom, and G. Aston-Jones: Nucleus locus ceruleus: New evidence of anatomical and physiological specificity. Physiol. Rev. 63: 844–914, 1983.
52. S. J. Grant. Y. H. Huang, and D. E. Redmond, Jr.: Benzodiazepines attenuate single unit activity in the locus coeruleus. Life Sci. 27: 2231–2236, 1980.
53. S. Siegel: Classical conditioning, drug tolerance, and drug dependence. In; Research Advances in Alcohol & Drug Problems. Vol. 7. R. G. Smart, F. B. Glaser, Y. Israel, H. Kalant, R. E. Popham, w. Schmide eds. Plenum Press, New York, 1983, pp 207–246.
54. S. Siegel. R. E. Hinson, M. D. Krank, and J. McCully: Heroin "overdose" death: The contriution of drug-associated environmental cues. Science 216: 436, 1982.

What is claimed is:

1. A method of preventing in a human subject accustomed to smoking tobacco the withdrawal symptoms associated with the cessation or reduction of tobacco smoking comprising administering to the subject an effective symptom preventing amount of alprazolam.

2. The method of claim 1, wherein the alprazolam is administered orally.

3. The method of claim 1, wherein the effective amount is an amount from about 0.1 to 10 mg administered daily.

4. The method of claim 3, wherein the effective amount is an amount from about 0.5 to 2.0 mg administered daily.

5. The method of claim 1, wherein the daily amount is administered in two or three doses.

6. The method of claim 5, wherein each succeeding dose is administered about 4 to 8 hours after the preceding dose.

7. The method of claim 1, wherein alprazolam is administered for about 3 to 6 weeks.

* * * * *